US010828497B2

(12) United States Patent
Barry et al.

(10) Patent No.: US 10,828,497 B2
(45) Date of Patent: Nov. 10, 2020

(54) METHOD OF MAKING AN ENCAPSULATED FILTERED FEEDTHROUGH FOR AN IMPLANTABLE MEDICAL DEVICE

(71) Applicant: Cardiac Pacemakers, Inc., St. Paul, MN (US)

(72) Inventors: Patrick J. Barry, North St. Paul, MN (US); Randy White, Blaine, MN (US); Steven A. Kubow, Hugo, MN (US); Scott A. Spadgenske, Buffalo, MN (US); David A. Chizek, Brooklyn Park, MN (US); Jerald Sauber, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 280 days.

(21) Appl. No.: 15/934,355

(22) Filed: Mar. 23, 2018

(65) Prior Publication Data
US 2018/0207428 A1 Jul. 26, 2018

Related U.S. Application Data

(62) Division of application No. 15/080,122, filed on Mar. 24, 2016, now Pat. No. 9,937,354.
(Continued)

(51) Int. Cl.
*H05K 3/30* (2006.01)
*A61N 1/375* (2006.01)
(Continued)

(52) U.S. Cl.
CPC ............. *A61N 1/3754* (2013.01); *H01G 4/35* (2013.01); *H03H 3/00* (2013.01); *H03H 7/17* (2013.01);
(Continued)

(58) Field of Classification Search
CPC .... A61N 1/3754; H05K 5/0247; H05K 3/303; H05K 3/22; H05K 2201/10015;
(Continued)

(56) References Cited

U.S. PATENT DOCUMENTS 4,594,641 A * 6/1986 Hernandez ............. H01G 4/228
174/72 B
6,437,664 B1 8/2002 Meppelink et al.
(Continued)

FOREIGN PATENT DOCUMENTS

WO WO-2016160514 A1 10/2016

OTHER PUBLICATIONS

"U.S. Appl. No. 15/080,122, Non Final Office Action dated Jul. 10, 2017", 9 pgs.
(Continued)

*Primary Examiner* — Paul D Kim
(74) *Attorney, Agent, or Firm* — Schwegman Lundberg & Woessner, P.A.

(57) ABSTRACT

An encapsulated filtered feedthrough assembly for an implantable medical device including a ferrule, an electrical insulator coupled to the ferrule, a printed circuit board (PCB), a feedthrough conductor extending through the electrical insulator and the PCB, and a capacitor coupled to the PCB. The encapsulated filtered feedthrough assembly can include a mold defining an opening and located with respect to the printed circuit board such that at least a portion of the capacitor is positioned within the opening. A first non-conductive material can underfill the capacitor and a second non-conductive material can be backfilled into the mold to encapsulate the capacitor.

10 Claims, 8 Drawing Sheets

Related U.S. Application Data

(60) Provisional application No. 62/140,606, filed on Mar. 31, 2015.

(51) Int. Cl.

| | |
|---|---|
| *H05K 1/18* | (2006.01) |
| *H01G 4/35* | (2006.01) |
| *H03H 3/00* | (2006.01) |
| *H03H 7/01* | (2006.01) |
| *H05K 1/02* | (2006.01) |
| *H05K 3/10* | (2006.01) |
| *H05K 3/22* | (2006.01) |
| *H05K 5/02* | (2006.01) |
| *H05K 3/28* | (2006.01) |

(52) U.S. Cl.
CPC .......... *H05K 1/0213* (2013.01); *H05K 1/184* (2013.01); *H05K 3/10* (2013.01); *H05K 3/22* (2013.01); *H05K 3/303* (2013.01); *H05K 5/0247* (2013.01); *H05K 3/284* (2013.01); *H05K 2201/10015* (2013.01); *H05K 2201/10189* (2013.01); *H05K 2201/10303* (2013.01)

(58) Field of Classification Search
CPC ....... H05K 1/0213; H05K 2201/10303; H05K 3/10; H05K 1/184; H05K 3/284; H05K 2201/10189; H03H 3/00; H03H 7/17; H01G 4/35

See application file for complete search history.

(56) References Cited

U.S. PATENT DOCUMENTS

| | | | |
|---|---|---|---|
| 7,187,535 | B1 | 3/2007 | Iyer et al. |
| 7,449,032 | B2 * | 11/2008 | Vaisman ................ H01G 2/065 29/25.03 |
| 7,719,854 | B2 | 5/2010 | Youker et al. |
| 9,521,744 | B2 * | 12/2016 | Barry ....................... A61N 1/08 |
| 2005/0024837 | A1 | 2/2005 | Youker et al. |
| 2006/0028784 | A1 | 2/2006 | Brendel |
| 2007/0203529 | A1 * | 8/2007 | Iyer ....................... A61N 1/3754 607/37 |
| 2007/0203530 | A1 | 8/2007 | Hubing et al. |
| 2015/0245468 | A1 | 8/2015 | Barry et al. |
| 2016/0287883 | A1 | 10/2016 | Barry et al. |

OTHER PUBLICATIONS

"U.S. Appl. No. 15/080,122, Notice of Allowance dated Nov. 22, 2017", 8 pgs.
"U.S. Appl. No. 15/080,122, Response filed May 15, 2017 to Restriction Requirement dated Mar. 14, 2017", 11 pgs.
"U.S. Appl. No. 15/080,122, Response filed Oct. 10, 2017 to Non Final Office Action dated Jul. 10, 2017", 12 pgs.
"U.S. Appl. No. 15/080,122, Restriction Requirement dated Mar. 14, 2017", 7 pgs.
"Application Serial No. PCT/US2016/024028, Invitation to Pay Add'l Fees and Partial Search Rpt dated May 31, 2016", 6 pgs.
"Australian Application Serial No. 2016243089, First Examination Report dated Dec. 5, 2017", 3 pgs.
"International Application Serial No. PCT/US2016/024028, International Search Report dated Aug. 22, 2016", 6 pgs.
"International Application Serial No. PCT/US2016/024028, Written Opinion dated Aug. 22, 2016", 7 pgs.

* cited by examiner

METHOD OF MAKING AN ENCAPSULATED FILTERED FEEDTHROUGH FOR AN IMPLANTABLE MEDICAL DEVICE

CLAIM OF PRIORITY

This application is a divisional of U.S. application Ser. No. 15/080,122, filed Mar. 24, 2016, now U.S. Pat. No. 9,937,354, which claims the benefit of priority under 35 U.S.C. § 119(e) of U.S. Provisional Patent Application Ser. No. 62/140,606, filed on Mar. 31, 2015, which is herein incorporated by reference in its entirety.

TECHNICAL FIELD

The present disclosure relates generally to medical devices and, in particular, to encapsulated filtered feedthrough assemblies for implantable medical devices.

BACKGROUND

Implantable medical devices (IMDs) are implantable or partially implantable. Some examples of IMDs include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The devices can be implanted subcutaneously and can include electrodes that are able to sense cardiac signals without being in direct contact with the patient's heart. Other examples of IMDs include implantable diagnostic devices, implantable drug delivery systems, or implantable devices with neural stimulation capability (e.g., vagus nerve stimulator, baroreflex stimulator, carotid sinus stimulator, deep brain stimulator, sacral nerve stimulator, etc.).

IMDs can include circuitry mounted within a hermetically-sealed device housing. The circuitry can be operatively connected to a lead which is implanted on or in the heart. The circuitry can be used for, for example, generating electrical signals that are delivered to the patient's heart through one or more feedthrough conductors that pass from the interior of the device housing to the exterior of the device housing. The feedthrough assembly provides a mechanism for electrical signal transfer through the hermetically sealed device housing. This hermetic seal serves to isolate the circuitry within the metal case from tissue, blood, and other patient fluid.

In addition to the electrical signals generated by the circuitry of the IMD, externally generated electromagnetic signals can also pass through the hermetic seal via the feedthrough assembly and interfere with proper operation of the implantable medical device. Thus, electromagnetic interference filters can be integrated into IMDs to filter these externally generated electromagnetic signals to maintain the intended voltage levels along the feedthrough conductors.

SUMMARY

The present disclosure is directed toward encapsulated filtered feedthrough assemblies, IMDs including the encapsulated filtered feedthrough assembly, and methods for making the same. The present inventors have recognized, among other things, that existing filtered feedthrough assemblies include high voltage capacitors that are densely packaged in a confined space. However, having high voltage capacitors in such confined spaces can promote high electrical field intensities, which can lead to the dielectric breakdown of air surrounding the high voltage components (e.g., capacitors) and can result in arcing, failure, and the loss of therapy delivery to a patient.

The encapsulated filtered feedthrough assemblies of the present disclosure can provide protection from the detrimental effects of concentrated electrical fields and mitigate high voltage breakdown failures of air gaps between components. The present inventors have recognized that encapsulating the capacitors with non-conductive materials can provide an encapsulated filtered feedthrough assembly that provides a high degree of dielectric isolation and can mitigate the high electric field breakdown issues associated with electric field compression in confined spaces. Further, non-conductive materials encapsulating the capacitors provide a higher voltage breakdown threshold than compared to air and the encapsulated filtered feedthrough assemblies can be used to facilitate designs with tighter spacing and therefore smaller size.

To better illustrate the encapsulated filtered feedthrough assemblies, IMDs including the encapsulated filtered feedthrough assemblies, and methods disclosed herein, a non-limiting list of examples is provided here:

Example 1 can include subject matter (such as a device) comprising a ferrule configured to be attached to a device container of the implantable medical device; an electrical insulator coupled to the ferrule by a connection element; a printed circuit board; a feedthrough conductor extending through the electrical insulator and the printed circuit board; a capacitor electrically coupled to the printed circuit board, wherein a gap is formed between the capacitor and the printed circuit board; a first non-conductive material disposed at least partially within the gap; a mold defining an opening and located with respect to the second side of the printed circuit board such that at least a portion of the capacitor is positioned within the opening; and a second non-conductive material disposed within the mold, the second non-conductive material encapsulating at least a portion of the capacitor.

In Example 2, the subject matter of Example 1 can optionally include a plurality of feedthrough conductors extending through the printed circuit board; and a plurality of capacitors each associated with one of the plurality of feedthrough conductors, wherein the mold includes a plurality of openings such that at least one capacitor is positioned at least partially within a corresponding opening.

In Example 3, the subject matter of one or both of Examples 1 and 2 can optionally include where at least two layers of the second non-conducting material and a portion of the mold are positioned between two adjacent capacitors.

In Example 4, the subject matter of one or any combination of Examples 1-3 optionally includes where a height of the mold extends beyond a height of the capacitor.

In Example 5, the subject matter of one or any combination of Examples 1-4 can optionally include where the first non-conductive material and the second non-conductive material are a different type of material from the mold.

In Example 6, the subject matter of one or any combination of Examples 1-5 can optionally include where the first non-conductive material and the second non-conductive material include a curable epoxy resin and the mold includes silicone.

In Example 7, the subject matter of one or any combination of Examples 1-6 can optionally include where the printed circuit board is a multi-layer circuit board.

Example 8 can include subject matter (such as a device), or can optionally be combined with the subject matter of one or any combination of Examples 1-7 to include such subject matter, comprising a device container including an electronic module within the device container; a header including a header core and a header shell disposed around the header core, wherein at least one electrical contact is positioned within the header core; a feedthrough assembly configured to electrically couple the electronic module within the device container to at least one electrical contact, the feedthrough assembly including: a capacitor electrically coupled to a printed circuit board, wherein a gap is formed between the capacitor and the printed circuit board; a first non-conductive material disposed at least partially within the gap; a mold defining an opening and located with respect to the printed circuit board such that at least a portion of the capacitor is positioned within the opening; and a second non-conductive material disposed within the mold, the second non-conductive material encapsulating at least a portion of the capacitor.

In Example 9, the subject matter of Example 8 can optionally include where the feedthrough assembly further includes: a ferrule configured to be attached to the device container; an electrical insulator coupled to the ferrule by a first connection element; a plurality of feedthrough conductors extending through the printed circuit board and the electrical insulator, the plurality of feedthrough conductors coupled to the electrical insulator by a second connection element; and a plurality of capacitors each associated with one of the plurality of feedthrough conductors, wherein the mold includes a plurality of openings such that at least one capacitor is positioned at least partially within a corresponding opening.

In Example 10, the subject matter of one or any combination of Example 8 or Example 9 can optionally include where at least two layers of the second non-conducting material and a portion of the mold are positioned between two adjacent capacitors.

In Example 11, the subject matter of one or any combination of Examples 8-10 can optionally include where the first non-conductive material and the second non-conductive material are a different type of material from the mold.

Example 12 the subject matter of one or any combination of Examples 8-11 can optionally include where the first non-conductive material and the second non-conductive material include a curable epoxy resin and the mold includes silicone.

Example 13 can include subject matter (such as a method), or can optionally be combined with the subject matter of one or any combination of Examples 1-12 to include such subject matter, comprising coupling a capacitor to a printed circuit board, wherein a gap is formed between a first surface of the printed circuit board and a second surface of the capacitor; disposing a feedthrough conductor through the printed circuit board; introducing a first non-conductive material into the gap to at least partially underfill the capacitor with the first non-conductive material; locating a mold with respect to the printed circuit board, the mold including an opening configured to receive at least a portion of the capacitor when the mold is in location with respect to the printed circuit board; and introducing a second non-conductive material into the mold to encapsulate at least a portion of the capacitor.

In Example 14, the subject matter of Examples 13 can optionally include coupling the capacitor to the printed circuit board including coupling a plurality of capacitors to the printed circuit board, and wherein the mold includes a plurality of openings, each opening separate from each other and configured to receive at least a portion of at least one corresponding capacitor of the plurality of capacitors when the mold is in location with respect to the printed circuit board.

In Example 15, the subject matter of one or any combination of Example 13 or Example 14 can optionally include coupling the conductor to at least one of the printed circuit and an electrical insulator; and coupling the mold to the printed circuit board using the first non-conductive material.

In Example 16, the subject matter of one or any combination of Examples 13-15 can optionally include curing the first non-conductive material; and curing the second non-conductive material.

In Example 17, the subject matter of one or any combination of Examples 13-16 can optionally include introducing the first non-conductive material onto the first surface of the printed circuit board; and allowing the first non-conductive material introduced onto the printed circuit board to be wicked into the gap.

In Example 18, the subject matter of one or any combination of Examples 13-17 can optionally include where the mold is formed of a third non-conductive material.

In Example 19, the subject matter of Example 18 can optionally include where the first non-conductive material and the second non-conductive material are a different type of material from the third non-conductive material.

In Example 20, the subject matter of Example 18 can optionally include where the third non-conductive material include silicone and the first non-conductive material and the second non-conductive material include a curable epoxy resin.

Example 21 can include, or can optionally be combined with any portion or combination or any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

These and other examples and features will be set forth in part in the following Detail Description. This Summary is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

Figure 1:
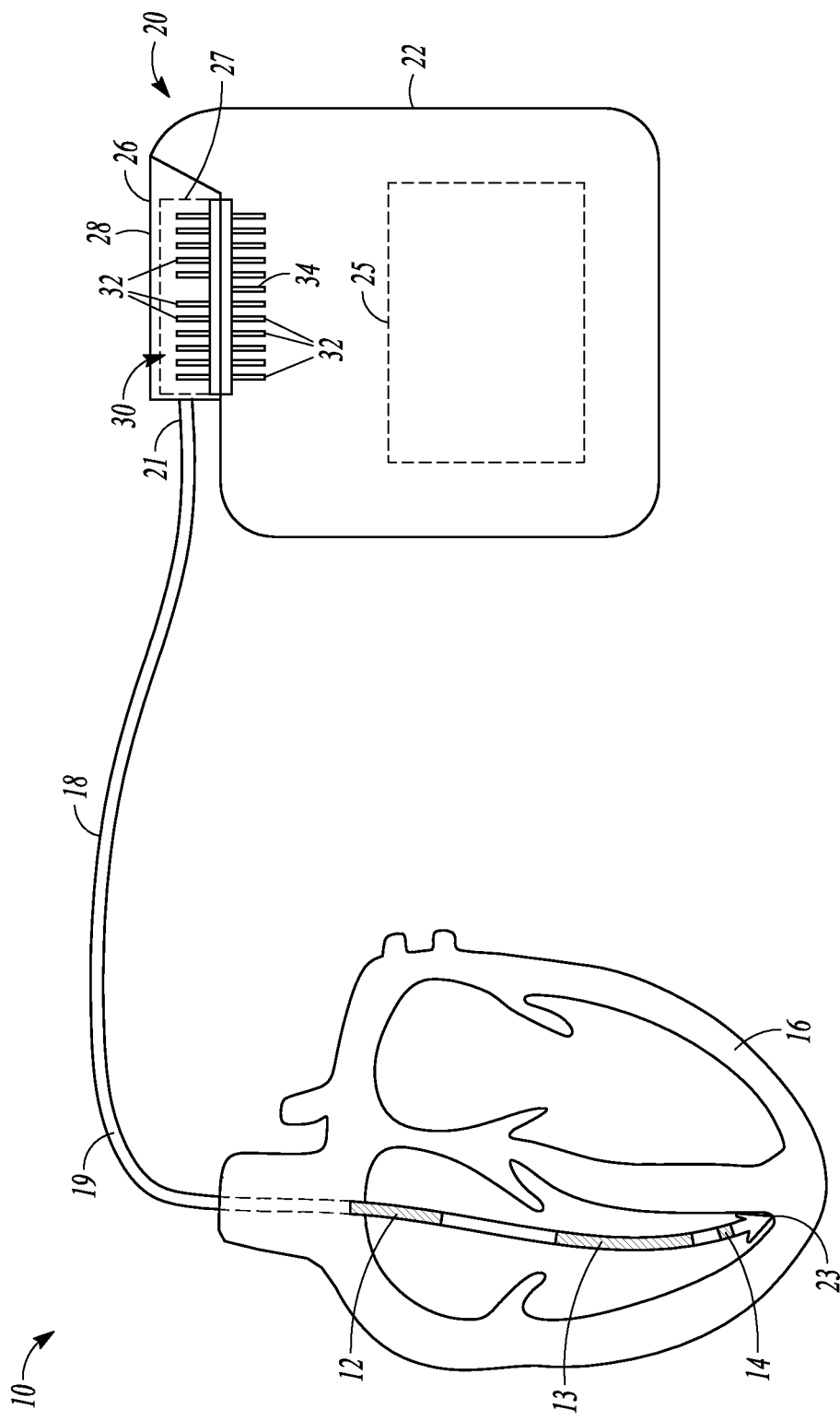
FIG. 1 illustrates an example of an implantable medical device (IMD).

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

In the following detailed description, reference is made to the accompanying drawings which form a part hereof, and specific embodiments in which the disclosure may be practiced are shown by way of illustration. It is to be understood that other embodiments may be used and structural changes may be made without departing from the scope of the present disclosure.

The present disclosure is directed toward an encapsulated feedthrough assembly for, for example, IMDs that include a printed circuit board (PCB) with at least one capacitor electrically coupled to the PCB. The encapsulated feedthrough assembly can include a first non-conductive material disposed at least partially within a gap formed between the PCB and the at least one capacitor. The feedthrough assembly can further include a mold that defines an opening and is located with respect to the printed circuit board such that at least a portion of the capacitor is positioned within the opening when the mold is coupled to the PCB. In an example, a second non-conductive material can be disposed within the mold to encapsulate at least a portion of the capacitor. The first and second non-conductive materials, along with the mold, can encapsulate the capacitor and provide a high voltage breakdown threshold and can be used to reduce the detrimental effects of concentrated electric fields.

FIG. 1 illustrates an example of an 1 MB 10. The 1 MB 10 can include an electronics unit, such as a pulse generator 20 and at least one lead 18. The pulse generator 20 can be, for example, implanted into a subcutaneous pocket made in the upper pectoral region of a patient. Alternatively, the pulse generator 20 can be placed in a subcutaneous or submuscular pocket made in the abdomen, or in other locations of the patient.

The pulse generator 20 generally includes a hermetically sealed device housing 22 including an electronic module 25 and a header 26. The header 26 can include a header core 27 and a header shell 28 disposed around the header core 27. The header 26 can be mechanically and electrically coupled to the device housing 22. The electronic module 25 can include a power supply such as a battery, a capacitor, and other components housed in the device housing 22. The pulse generator 20 can also include electrical circuitry, such as a microprocessor, to provide processing, evaluation, or to determine and deliver electrical shocks or pulses of different energy levels or timing for defibrillation, cardioversion, or pacing to a heart such as in response to cardiac arrhythmia including fibrillation, tachycardia, heart failure, and bradycardia.

In some examples, the pulse generator 20 can include an antenna within the header 26 configured to wirelessly transfer information electromagnetically to an external module. The external module can include a physician programmer, a bedside monitor, or other relatively nearby assembly used to transfer programming instructions or configuration information to the implantable pulse generator 20, or to receive diagnostic information, a disease status, information about one or more physiologic parameters, or the like, from the pulse generator 20. The external module can be communicatively connected to one or more other external assemblies, such as a remote external assembly, located elsewhere (e.g., a server, a client terminal such as a web-connected personal computer, a cellular base-station, or another wirelessly-coupled or wired remote assembly).

The at least one lead 18 can include a lead body 19 having a proximal end 21, where the lead 18 can be coupled to the header 26 of the pulse generator 20. The lead 18 can extend to a distal end 23, which can be coupled with a portion of a heart 16, when implanted. The distal end 23 of the lead 18 can include one or more electrodes 12, 13, 14. The one or more electrodes 12, 13, 14 can be located medially or at other locations along the lead 18. At least one electrical conductor can be disposed within the lead 18, such as to extend from the proximal end 21 to at least one respective electrode(s) 12, 13, 14. The electrical conductors carry electrical current and pulses between the pulse generator 20 and the electrode(s) 12, 13, 14.

In the example illustrated in FIG. 1, the lead 18 can include defibrillation electrodes, such as for delivering defibrillation therapy via a first defibrillation electrode, for example, electrode 12 and/or a second defibrillation, for example, electrode 13. The lead 18 can include additional electrodes, such as for delivering pacing therapy via a pacing/sensing electrode 14. In various examples, the lead 18 can also include an additional tip electrode at the distal end thereof, which in conjunction with the pacing/sensing electrode, for example, electrode 14 can provide for bi-polar pacing and sensing capabilities. While the example in FIG. 1 includes one lead and three electrodes configured to be positioned within the heart, the number and location of the leads and electrodes can vary depending on the type of therapy to be provided and the type of IMD.

In the example shown in FIG. 1, the lead 18 is shown extending into the right ventricle of the heart 16. In other examples, additional leads can be coupled to the pulse generator 20 for implantation within, for example, the right atrium and/or the coronary venous system (e.g., for pacing/sensing of the left ventricle in a bi-ventricular pacing scheme).

In some examples, the IMD 10 can be suitable for use as or with one or more implantable electrical stimulators, such as, but not limited to, pulse generators, neuro-stimulators, skeletal stimulators, central nervous system stimulators, or stimulators for the treatment of pain. The system can also be utilized as a sensor or a receiver. The electrodes can be used, for sensing, pacing, and/or shocking, for example.

An example of an encapsulated feedthrough assembly 30 (also referred to herein as "feedthrough assembly 30") is schematically shown in FIG. 1. The feedthrough assembly 30 can be attached to a hole in the device housing 22 and is attached so that the device housing 22 is hermetically sealed. The feedthrough assembly 30 can include a plurality of feedthrough conductors 32 mounted within and extending from an interior of the device housing 22 to an exterior of the device housing 22. The feedthrough assembly 30 can further include a ground wire 34 directly attached to a ferrule (see ferrule 36 in FIG. 2). The ground wire 34, in an example, can be located and attached to electronics on the interior side of the device housing 22 and is not exposed on the exterior side of the device housing 22.

Figure 2:
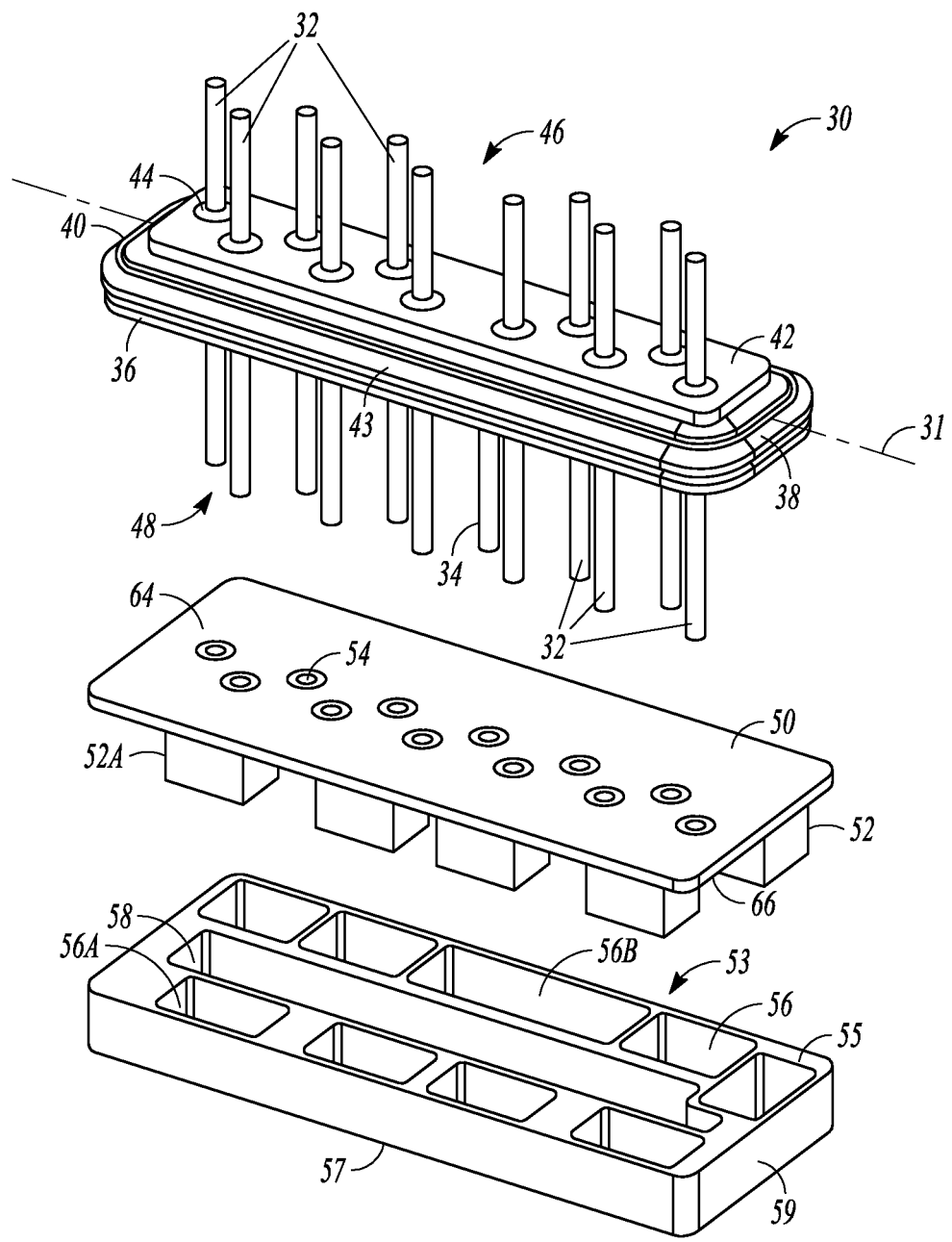
FIG. 2 illustrates an expanded view of an example of a portion of the encapsulated feedthrough assembly.

FIG. 2 illustrates an example of an expanded view of a portion of the encapsulated feedthrough assembly 30. The feedthrough assembly 30 can include an elongate metallic ferrule 36 (also referred to herein as "ferrule 36") having a longitudinal axis 31, a first end 38, a second end 40, and a central portion 43 located between the first end 38 and the second end 40. The ferrule 36 can be mounted to the device housing 22 (shown in FIG. 1) of the IMD 10 by fitting the ferrule 36 into a hole in the device housing 22 and laser welding the ferrule 36 at an outer perimeter of the ferrule 36. In some examples, the ferrule 36 can be formed of titanium. In other examples, the ferrule 36 can be formed of other metallic materials.

The feedthrough assembly 30 can include an electrical insulator 42 (also referred to herein as "insulator 42"), which may be mounted within or coupled to the ferrule 36, for example, using gold brazing techniques. The electrical insulator 42 can include a plurality of holes 44 extending through the insulator 42 through which the feedthrough conductors 32 may pass. In some examples, the electrical insulator 42 can include, but is not limited to, ceramics, glass, and plastics. As shown in FIG. 2, the feedthrough assembly 30 can include a plurality of feedthrough conductors 32. The feedthrough conductors 32 can be mounted within and extend through a respective feedthrough hole 44 so as to extend from an exterior side 46 to an interior side 48 of the feedthrough assembly 30.

The feedthrough conductors 32 can be hermetically connected to the electrical insulator 42 at the holes 44, for example, using a gold-brazed joint, soldered joint, welded joint, or other coupling methods providing a hermetic connection between the feedthrough conductors 32 and the electrical insulator 42. The feedthrough conductors 32 can operate to electrically couple the electrodes 12, 13, 14 (shown in FIG. 1) of lead 18 to the pulse generator circuitry within the inner region defined by the device housing 22 of the pulse generator 20. In various examples, the feedthrough conductors 32 can be pins, wires (e.g., palladium and its alloys, platinum and its alloys, titanium, molybdenum, or gold-plated wires), or a combination thereof.

In some examples, the ground wire 34 can be directly attached to the central portion 43 of the ferrule 36. In other examples, the ground wire 34 can be electrically coupled to the ferrule 36 by welding or brazing. In some examples, the ground wire 34 and/or the ground pin can comprise a circuit trace, weld, brazing joint, via, electrically conductive epoxy resin, or any other conductive material configured to provide an electrical ground to the feedthrough assembly 30. In certain examples, the ground wire 34 and/or ground pin can be centrally located along feedthrough assembly 30 with respect to the plurality of feedthrough wires 32. In an example, the ground wire 32 does not pass through or alongside the insulator 42. The ground wire 32 can be located on the interior side 48 and is not exposed on the exterior side 46 and thus does not require hermetic connection. Furthermore, though a single ground wire 34 is shown, a plurality of ground wires 34 and/or ground pins can be provided in the feedthrough assembly 30 to provide parallel ground paths for electromagnetic signals to be filtered. In various examples, the ground wire 34 and/or ground pin can be omitted.

As illustrated in FIG. 2, the feedthrough assembly 30 can include a printed circuit board (PCB) 50 and a plurality of capacitors 52. The PCB 50 can include a plurality of holes 54 extending therethrough. When assembled, the feedthrough conductors 32 can be positioned through the holes 54 of the PCB 50. The PCB 50 can provide the electrical coupling between the capacitors 52 and the feedthrough conductors 32 via electrical traces on the PCB 50 that are electrically coupled to a conductor terminal on each capacitor 52.

In some examples, the PCB 50 can be a multi-layer PCB including a plurality of ground layers separated by suitable insulating layers. For example, the multi-layer PCB can have three ground layers and three insulating layers, though any number of ground layers or insulating layers are contemplated by the present disclosure. Additionally, in some examples utilizing one or more ground pins, the PCB 50 can include the same number of ground pins as the number of ground layers in the multi-layer PCB.

In an example, the PCB 50 can include a multilayer FR4 PCB. Insulating layers can include any electrical insulating material or dielectric, such as, but not limited to, FR4, epoxy glass, polyimide, silicates, or the like. Additionally, the ground layers of the multilayer PCB can include layers of conductive material, which may include any conductive material, such as, but not limited to copper, or any other conductive metal or semiconductor. In some examples, one or more layers of aluminum foil may be laminated to one or both sides of an insulating material (e.g., FR4 material) to form alternating ground and insulating layers.

In some examples, the capacitors 52 can have a breakdown voltage that is configured to withstand defibrillation or electrocautery voltages that may be introduced to the feedthrough assembly 30. For example, the capacitors 52 can have a breakdown voltage in the range of 400 volts to 2000 volts, such as a breakdown voltage of about 1000 volts. Furthermore, capacitors 52 can be ceramic capacitors and be configured to be surface-mounted to the PCB 50 and/or wire-mounted or soldered thereto. Additionally, the capacitors 52 can have a capacitance value configured to filter signals having a particular frequency. For example, in some examples, capacitors 52 can have capacitance values configured to attenuate signals having frequencies in a band utilized, for example, in mobile telephones or magnetic resonance imaging processes.

As discussed herein, a gap can be formed between the capacitors 52 and the PCB 50 when the capacitors 52 are coupled to the PCB 50. A first non-conductive material can be disposed within the gap. Underfilling the capacitors 52 with the first non-conductive material can minimize the air surrounding the capacitor and provide higher voltage breakdown threshold between adjacent components.

The feedthrough assembly 30 can include a mold 59. The mold 59 can define openings extending through the mold 59. For example, the mold 59 illustrated in FIG. 2 can include a plurality of openings 56 that are positioned along the sides of the mold 59 and extend from the top side 55 of the mold 59 to the bottom side 57 of the mold 59. When assembled, the openings 56 can be configured to receive at least a portion of at least one corresponding capacitor 52. In some examples, each opening along the side of the mold 59 can receive a single capacitor 52. For example, opening 56A can receive single capacitor 52A. In some examples, an opening 56 can be configured to receive more than one capacitor 52. For example, opening 56B can be configured to receive two capacitors 52. In an example where more than one capacitor 52 is positioned within a single opening 56, the capacitors 52 can be coupled to the PCB 50 such that there is no voltage potential difference between the capacitors 52, for example, when the same terminal (e.g., negative or positive) of the two capacitors 52 are adjacent to each other.

In an example, the mold 59 can also include an opening 58 that is an elongated opening positioned along the center of the mold 59. When assembled, the central opening 58 can be configured to receive the feedthrough conductors 34 that extend through the PCB 50. The opening 58 can be one single opening that can receive all of the feedthrough conductors or mold 59 can include a plurality of openings along the center of the mold 59 such that each opening in the center can receive one or more of the feedthrough conductors 34. Further, while openings 56 can be configured to receive one or more capacitors 52 and opening 58 can be configured to receive the feedthrough conductors 34, the mold 59 can be formed with openings configured to receive one or more of both capacitors 52 and feedthrough conductors 34.

As shown in FIG. 2, each opening 56, 58 can be distinct (e.g., separate) from the other openings 56, 58. By providing distinct openings 56, 58, the capacitors 52 can be fenced in and isolated from one another by at least one layer of the mold 59. While the example shown in FIG. 2 includes nine openings 56 located along the sides or perimeter of the mold 59 and one central opening 58, the number, location, and shape of the openings 56, 58 can vary based on the configuration of the capacitors 52, the feedthrough conductors 32, and ground wire 34.

The mold 59 can be formed of non-conductive materials. For example, the mold 59 can include, but is not limited to, silicone, epoxy resins, thermoplastics, thermoset plastics, and combinations thereof. In some examples, the mold 59 can be formed of a material that is flexible, such as, silicone. The flexibility of the mold 59 can assist in forming a tight seal between the PCB 50 and the mold 59.

As disused herein, the mold 59 can be coupled to the PCB 50. Once the capacitors 52 are coupled (e.g., soldered) to the PCB 50, the first non-conductive material can be used to underfill the capacitors 52. That is, the gap formed between the PCB 50 and the capacitors 52 can be filled with the first non-conductive material. As well as underfilling the capacitors 52, the first non-conductive material can also be used to couple the mold 59 to the PCB 50. As discussed herein, the mold 59 can act like a fence and each capacitor 52 can be positioned within a corresponding opening 56 and be surrounded by the mold 59. Once the mold 59 is coupled to the PCB 50, a second non-conductive material can be backfilled into the openings 56, 58 of the mold 59 to encapsulate the capacitors 52 and surround a portion of the feedthrough conductors 32 and ground pin 34. The underfilled and encapsulated capacitors 52, along with the mold 59, provide an encapsulated filtered feedthrough assembly with a high degree of dielectric isolation and can mitigate the high electric field breakdown issues associated with the electric field compression in confined spaces. While the mold 59 can provide shielding between capacitors 52, the first non-conductive material and the second non-conductive material used to underfill and encapsulate the capacitors 52 can act to further mitigate high voltage fields that may be present surrounding the capacitors 52. Thus, underfilling and encapsulating the capacitors 52 can minimize air gaps around the capacitors and increase the dielectric isolation.

Figure 3:
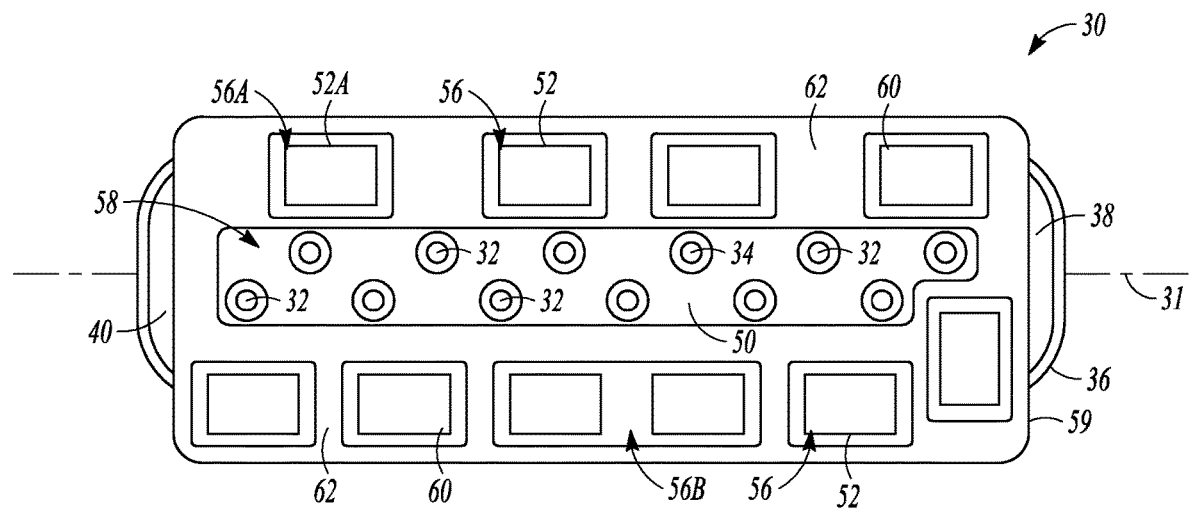
FIG. 3 illustrates a bottom view of an example of the portion of the encapsulated feedthrough assembly shown in FIG. 2.

FIG. 3 illustrates an example of a bottom view of the portion of the encapsulated feedthrough assembly 30 shown in FIG. 2. As illustrated in FIG. 3, the assembled portion of the encapsulated feedthrough assembly 30 includes the PCB 50 and the ferrule 36. The plurality of capacitors 52 can be coupled to the PCB 50 and underfilled with the first non-conductive material. The mold 59 can be coupled to the PCB 50 by, for example, the first non-conductive material used to underfill the plurality of capacitors 52. As shown in FIG. 3, the mold 59 can include openings 56, 58. One or more openings 56 can receive at least a portion of a single corresponding capacitor 52. For example, opening 56A can receive at least a portion of capacitor 52A and opening 56B can receive at least a portions of two capacitors 52.

As shown in FIG. 3, the opening 58 of the mold 59 can be an elongated central opening that can surround or fence in the area including the feedthrough conductors 32 and ground wire 34 extending through the PCB 50. While the opening 58 in FIG. 3 illustrates a single opening to receive all of the feedthrough conductors 32 and ground wire 34, other configurations are possible. For example, more than one central opening 58 can be formed in the mold 59 and can be configured to receive one or more feedthrough conductors 32 and/or ground wire 34.

In some examples, the mold 59 can be formed to include openings that receive one or more capacitors 52, one or more feedthrough conductors 32, and one or more of both capacitors 52 and feedthrough conductors 32. For example, the openings 56 of the mold 59 can be configured to receive a single capacitor 52, more than one capacitor 52, and one or more capacitors 52 and one or more feedthrough conductors 32.

As illustrated in FIG. 3, a space 60 can be defined between the capacitors 52 and the portion of the mold 59 defining the corresponding opening 56. The space 60 can receive the second non-conductive material to encapsulate the capacitors 52. Additionally, walls 62 of the mold 59 positioned between the openings 56 are also positioned between adjacent capacitors 52, which can shield one capacitor 52 from another.

Figure 4:
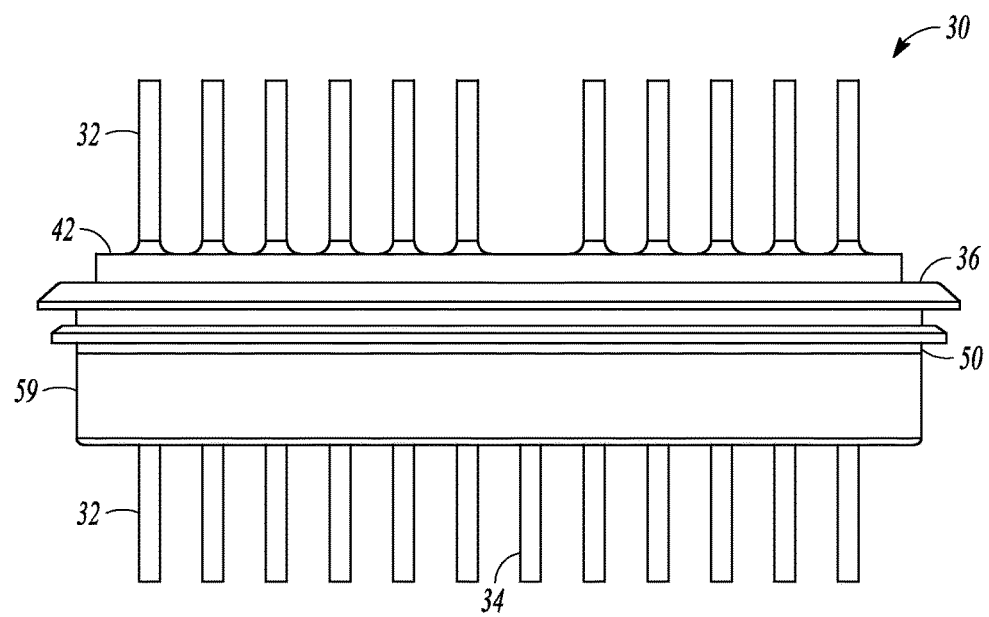
FIG. 4 illustrates a side view of an example of a portion of an encapsulated feedthrough assembly.

FIG. 4 illustrates a side view of an example of an encapsulated feedthrough assembly 30. As shown, the feedthrough assembly 30 can include the ferrule 36 coupled to an insulator 42. The PCB 50 can be coupled to the ferrule 36 and the mold 59. The feedthrough conductors 32 can extend through the PCB 50 and the mold 59, where the ground wire 34 does not extend through the insulator 42.

Figure 5:
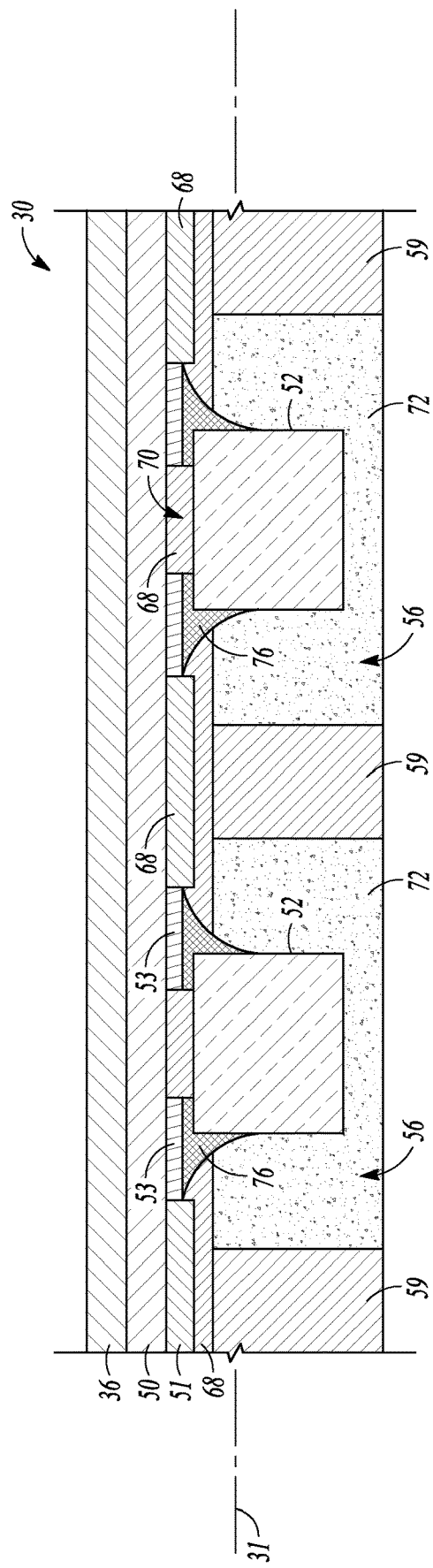
FIG. 5 illustrates a cross-sectional view of an example of the encapsulated feedthrough assembly.

FIG. 5 illustrates a cross-sectional view of an example of the encapsulated feedthrough assembly 30. The cross-sectional view in FIG. 5 is taken along a portion of the length of the feedthrough assembly parallel to the longitudinal axis of the feedthrough assembly including two adjacent capacitors 52. FIG. 5 differs from FIGS. 2-4, in that the example illustrated in FIG. 5 shows the first non-conductive material 68 that underfills the capacitors 52 and the second non-conductive material 72 that encapsulates the capacitors 52.

As discussed herein, the gap 70 can be formed between the capacitor 52 and the PCB 50. As shown in FIG. 5 and discussed herein, the gap 70 between the capacitor 52 and the PCB 50 has been filled with the first non-conductive material 68.

The PCB 50 can include a layer of soldermask 51 and component attachment surface pads 53 (e.g., copper pads). As discussed herein, a portion of the soldermask 51 can be removed along a surface of the PCB 50 to increase the gap 70 formed between the PCB 50 and the capacitor 52. Along with increasing the size of the gap 70, removing a portion of the soldermask 51 can also expose the component attachment surface pads 53 that are electrically coupled to the capacitors 54. For example, each capacitor 52 can include a positive terminal and a negative terminal such that when the capacitor is coupled to the PCB 50, one terminal is electrically coupled to one component attachment surface pad 53 and the other terminal is electrically coupled to the other contact pad 53.

The first non-conductive material 68 can be disposed at least partially within the gap 70 to underfill the capacitors 52 and fill the gap 70. "At least partially" as used herein, is defined as providing a sufficient amount of the first non-conductive material 68 such that the amount of continuous free air paths between metal features of different electrical potential is minimized. In other words, voids within the first non-conductive material 68 that expose metal to metal are minimized.

The capacitors 52 can be coupled to the PCB 50 via attachment element 76. In some examples, the attachment element 76 can be formed in a soldering operation using a conductive metal such as tin-lead or tin-lead-silver solder.

The first non-conductive material 68 can be used to couple the mold 59 to the PCB 50. For example, the first non-conductive material 68 can be disposed with the gap 70 as well as along a surface of the PCB 50 that is configured to be coupled to the mold 59. While the mold 59 is shown being coupled to a portion of the PCB 50 including the soldermask 51, the mold can be coupled to a location of the PCB that has the soldermask removed. The first non-conductive material can include, but is not limited to, epoxy resins, silicones, and cyanoacrylates. In some examples, the first non-conductive material can be a one part, heat curable, fast curing epoxy resin.

As shown in FIG. 5, the openings 56 defined by the mold 59 can each receive a corresponding single capacitor 52. In some examples, a single opening 56 can include one or more capacitors 52. As discussed herein, the openings 56 defined by the mold 59 can be backfilled with the second non-conductive material 72 to at least partially encapsulate the capacitors 52. As discussed herein with respect to the first non-conductive material, the second non-conductive material 72 is applied such that any continuous free air paths between metal features of different electric potentials are minimized, such as any voids exposing metal to metal.

In some examples, at least two layers of the second non-conductive material 72 and a portion of the mold 59 can be positioned between two adjacent capacitors 52. The second non-conductive material can include, but is not limited to, various epoxy resins, silicones, and molding compounds. In some examples, the second non-conductive material 72 can be a UV curable epoxy resin.

As shown in FIG. 5, the capacitors 52 can be underfilled and encapsulated by the first non-conductive material 68 and the second non-conductive material 72, where the openings 56 of the mold 59 can be positioned around the underfilled and encapsulated capacitors 52. The encapsulated feedthrough assembly 30 can completely encapsulate the capacitors 52 with the first and second non-conductive material (e.g., non-conductive epoxy resin) and can isolate the capacitors 52 from each other by use of mold 59 (e.g., non-conductive material such as silicone).

As discussed herein, the mold 59 can include a third non-conductive material. In an example, the first non-conductive material and the second non-conductive material can be a different type of material from the third non-conductive material. For example, the third non-conductive material can be silicone and the first non-conductive material and the second non-conductive material can be an epoxy resin.

The first, second, and third non-conductive materials can be selected for their electrical properties, which will be dependent on the voltage requirement for the particular application. For example, the first, second, and third non-conductive materials can have a resistivity, dielectric constant, and dielectric breakdown potential that is greater than air. In one example, the encapsulated feedthrough assembly can be used in high voltage applications, for example, including applications that have electrical potentials greater than 1000 Volts Direct Current. In that instance, the resistivity of one or more of the first, second, and third non-conductive materials, can have a resistance value greater than 100 Meghoms for each feedthrough conductor to any other feedthrough conductor. In an example, the dielectric constant of one or more of the first, second, and third non-conductive materials can be about 3, which is three times greater than air and the dielectric breakdown potential of one or more of the first, second, and third non-conductive materials can be greater than 500 volts/millimeter, whereas air is typically rated as about 75 volts/millimeter.

Further, while the first, second, and third non-conductive materials have a resistivity, dielectric property, and dielectric breakdown performance greater than air, other properties of the materials can be considered for their selection. For example, the first non-conductive material can have a low viscosity that facilitates free flow under the capacitor due to capillary flow and minimizes air gaps. The capillary effect ensures sufficient fill under the capacitor. In an example, the second non-conductive material can have a low viscosity and be UV curable, which can make the processing of the material fast, easy, and minimize air gaps. Further, the third non-conductive material can be made out of a flexible material, which can help with gasketing of the mold to the PCB.

The feedthrough assembly 30 of the present disclosure, including the first, second, and third non-conductive materials, can provide a high degree of dielectric isolation and can mitigate the high electric field breakdown issues associated with electric field compression in confined spaces.

Figure 6:
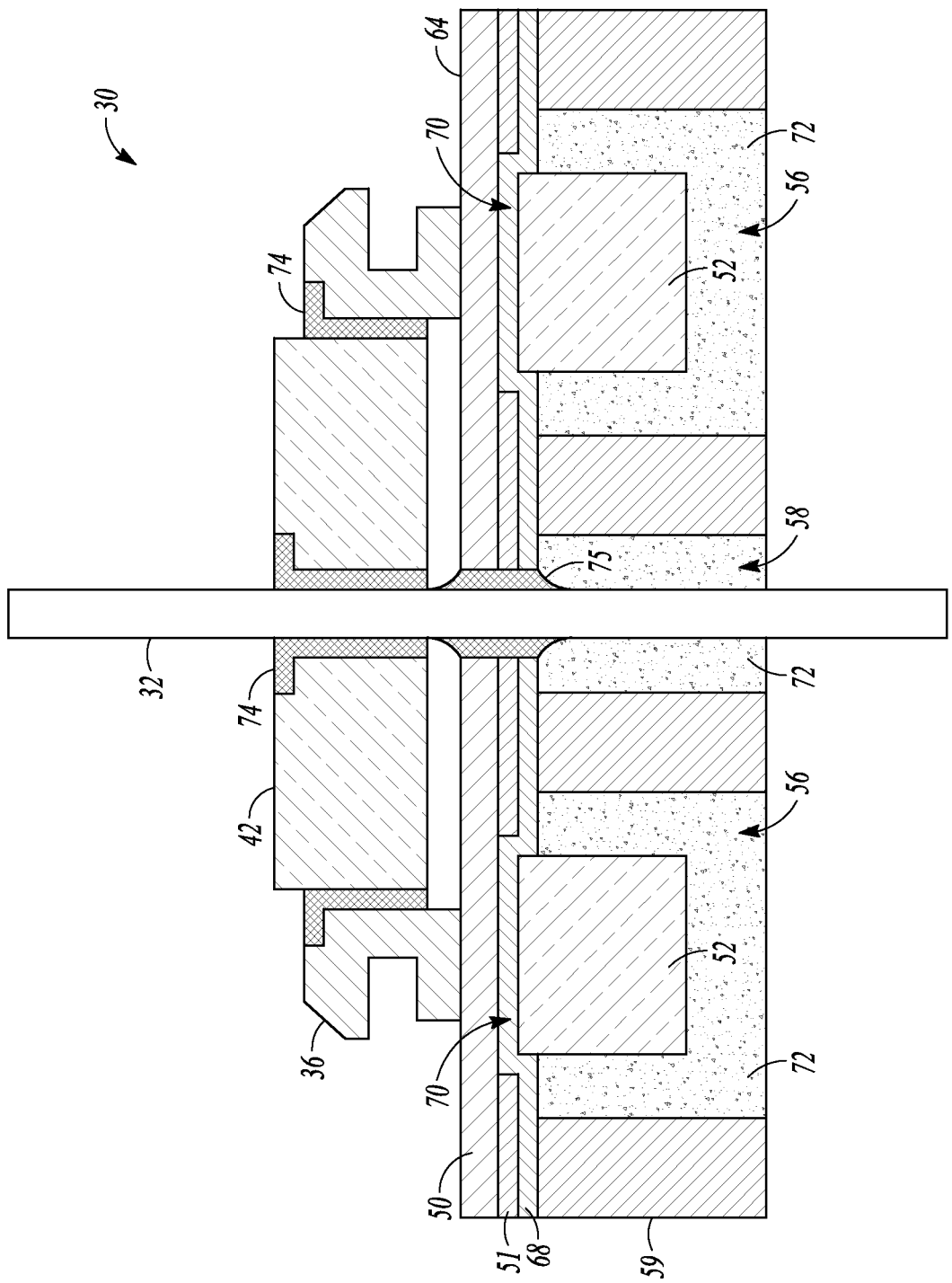
FIG. 6 illustrates another cross-sectional view of an example of the encapsulated feedthrough assembly.

FIG. 6 illustrates another cross-sectional view of an example of the encapsulated feedthrough assembly 30. The cross-sectional view in FIG. 6 is taken along a width of the feedthrough assembly perpendicular to a longitudinal axis of the feedthrough assembly 30. Similarly to FIG. 5, FIG. 6 differs from FIGS. 2-4, in that the example illustrated in FIG. 6 shows the first non-conductive material 68 that underfills the capacitors 52 and the second non-conductive material 72 that encapsulates the capacitors 52.

The insulator 42 can be attached to an inner surface of the ferrule 36 by an attachment element 74. In various examples, the attachment element 74 can be made of an electrically conductive material. In some examples, the attachment element 74 can be formed by a brazing operation using a conductive metal such as gold, alloys of gold, or others which form a hermetic bond between the insulator 42 and the inner surface of the ferrule 36. Similarly, the feedthrough conductor 32 can be attached to an inner surface of the insulator 42 and to the PCB 50. The feedthrough conductor 32 can be coupled to the insulator 42 via a brazing operation using the attachment element 74. The PCB 50 can be coupled to the feedthrough conductor 32 using attachment element 75. In some examples, the attachment element 75 can be formed in a soldering operation using a conductive metal such as tin-lead or tin-lead-silver solder.

As shown in FIG. 6, the feedthrough conductor 32 extends through a hole in the PCB 50. The hole (e.g., hole 54 shown in FIG. 2) extends from a top surface 64 of the PCB 50 to a bottom surface 66 of the PCB 50.

As discussed herein, a gap 70 can be formed between the capacitor 52 and the PCB 50. As shown in FIG. 6, the gap 70 between the capacitor 52 and the PCB 50 has been filled with the first non-conductive material 68. In some examples, the PCB 50 can include a layer of soldermask 51 that has been removed along portions of the PCB 50. The soldermask 51 can be removed in certain areas to increase the gap 70. The first non-conductive material 68 can be disposed at least partially within the gap 70. The first non-conductive material 68 can also be deposited onto a surface of the PCB 50 to be used to couple the mold 59 to the PCB 50. While the mold 59 is shown being coupled to a portion of the PCB 50 including the soldermask 51, the mold 59 can be coupled to a location of the PCB 50 that has the soldermask 51 removed. As shown in FIG. 6, the openings 56 defined by the mold 59 each receive a corresponding single capacitor 52. Additionally, the opening 58 defined by the mold 59 can receive a portion of the feedthrough conductor 32.

As discussed herein, once the mold 59 is coupled to the PCB 50, the openings 56, 58 of the mold 59 can be backfilled with the second non-conductive material 72 to at least partially encapsulate the capacitors 52 and the feedthrough conductor 32. As shown in FIG. 6, the capacitors 52 can be underfilled and encapsulated by the first non-conductive material 68 and the second non-conductive material 72, where the openings 56 of the mold 59 can be positioned around the underfilled and encapsulated capacitors 52.

Figure 7:
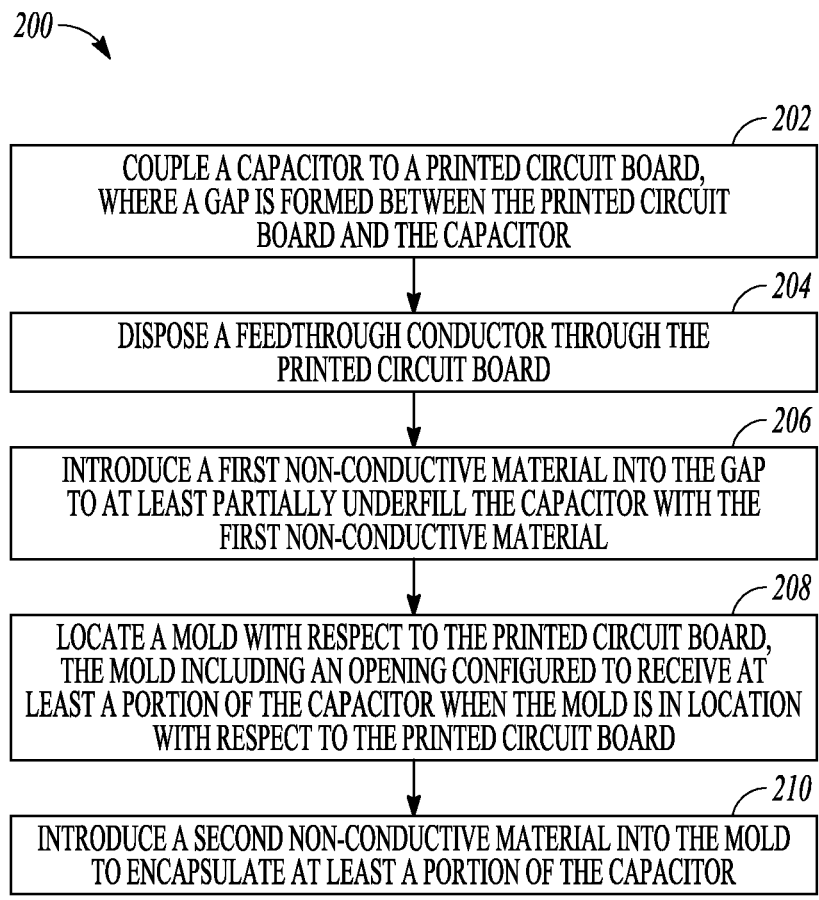
FIG. 7 shows a flow diagram of an example method of making an encapsulated filtered feedthrough assembly for an IMD.

FIG. 7 is a flow diagram of an example method 200 of making an encapsulated filtered feedthrough assembly for an implantable medical device. At step 202, the method 200 can include coupling a capacitor to a printed circuit board, where a gap is formed between a first surface of the printed circuit board and a second surface of the capacitor. For example, the capacitor 52 can be coupled to the PCB 50, where the gap 70 is formed between the PCB 50 and the capacitor 52, as shown in FIGS. 5 and 6.

At step 204, the method 200 can include disposing a feedthrough conductor through the PCB. For example, feedthrough conductor 32 can be disposed through the PCB 50 and the insulator 42, where the feedthrough conductor 32 can be coupled to the insulator 42 and the PCB 50, as shown in FIG. 6.

At step 206, the method 200 can include introducing a first non-conductive material into the gap to at least partially underfill the capacitor with the first non-conductive material. For example, the method 200 can include introducing the first non-conductive material 68 to underfill the capacitor 52, as shown in FIGS. 5 and 6.

At step 208, the method 200 can include locating a mold with respect to the PCB, the mold including an opening configured to receive at least a portion of the capacitor when the mold is in location with respect to the PCB. For example, the mold 59 can be located with respect to the PCB 50, where the mold 59 includes an opening 56 to receive at least a portion of the capacitor 52 when the mold 59 is in location with respect to the PCB 50. The method 200 can further include coupling the mold 59 to the PCB 50 by using the first non-conductive material 68. The method 200 can further include curing the first non-conductive material. For example, the mold 59 can be placed onto the PCB 50 and in contact with the first non-conductive material 68 and then subsequently cured to couple the mold to the PCB.

At step 210, the method 200 can include introducing or backfilling a second non-conductive material into the mold to encapsulate at least a portion of the capacitor. For example, the second non-conductive material 72 can be introduced into the mold 59 to encapsulate at least a portion of the capacitor 52, as shown in FIGS. 5 and 6. The mold 59 can be formed of a third non-conductive material, such as silicone. The method 200 can further include curing the second non-conductive material. In some examples, the second non-conductive material can be curable via UV light. In some examples, the mold 59 can be UV transparent to assist in the curing of the second non-conductive material.

Figure 8A:
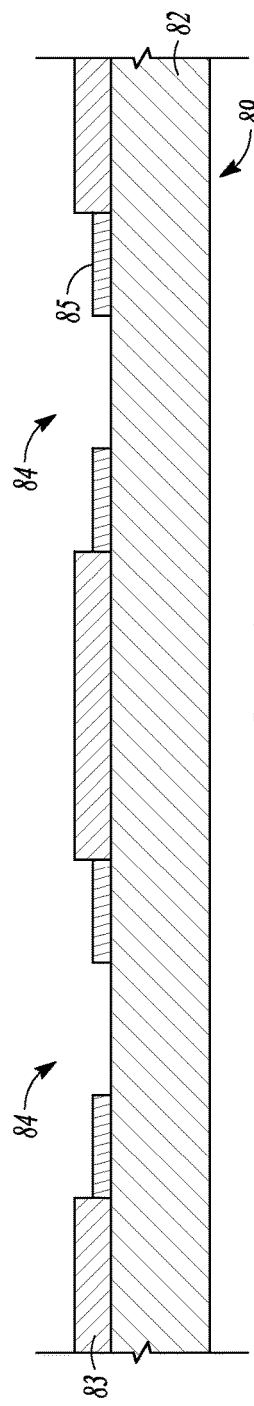
FIG. 8A illustrates an example of a printed circuit board (PCB).

FIGS. 8A-8E illustrates underfilling and encapsulating capacitors coupled to a PCB. FIG. 8A illustrates an example of a PCB 82. As shown in FIG. 8A, the PCB 82 can have a portion of a solder mask 83 removed along areas 84 of the PCB 82 and have component attachment surface pads 85. As discussed herein, a portion of the soldermask 83 can be removed to create a larger gap between a capacitor and the PCB, which is more suitable for underfilling the capacitors. Along with increasing the size of the gap, removing a portion of the soldermask 83 can also expose the component attachment surface pads 85.

Figure 8B:
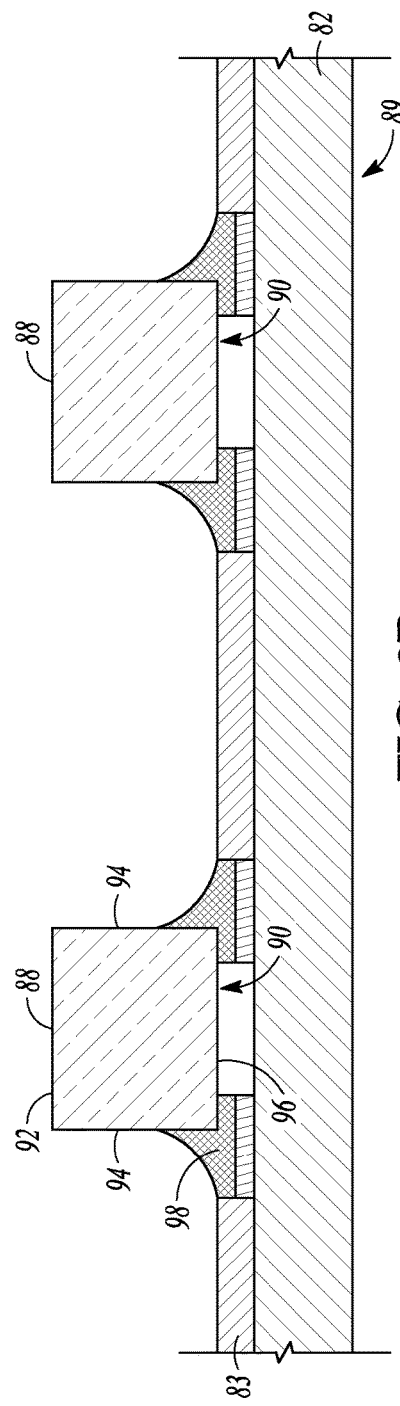
FIG. 8B illustrates an example of capacitors coupled to the PCB in FIG. 8A.

FIG. 8B illustrates an example of capacitors 88 coupled to the PCB 82 in FIG. 8A. The capacitors 88 can be coupled to the PCB 82 and can include a top surface 92, a bottom surface 96, and side surfaces 94. The capacitors 88 can be coupled to the PCB 82 with an attachment element 98 (e. g., solder) such that the attachment element 98 can be positioned along a portion of the bottom surface 96 and along a portion of the side surfaces 94 of the capacitors 88. The component attachment surface pads 85 can be electrically coupled to the capacitors 88. For example, each capacitor 88 can include a positive terminal and a negative terminal such that when the capacitor is coupled to the PCB 82, one terminal is electrically coupled to one component attachment surface pad 85 and the other terminal is electrically coupled to the other contact pad 85.

Gap 90 can be formed between the bottom surface 96 of the capacitor and the PCB 82. The gap 90 can be formed having a sufficient distance between the PCB 82 and the bottom surface 96 of the capacitor 88 to receive the underfill (e.g., the first non-conductive material). For example, the gap 90 can have a distance between the PCB 82 and the bottom surface 96 of the capacitor 88 that is within a range of about 1 thousandth of an inch (mil) to about 5 mils. In some examples, the gap 90 can be within a range of about 1 mil to about 3 mils.

Figure 8C:
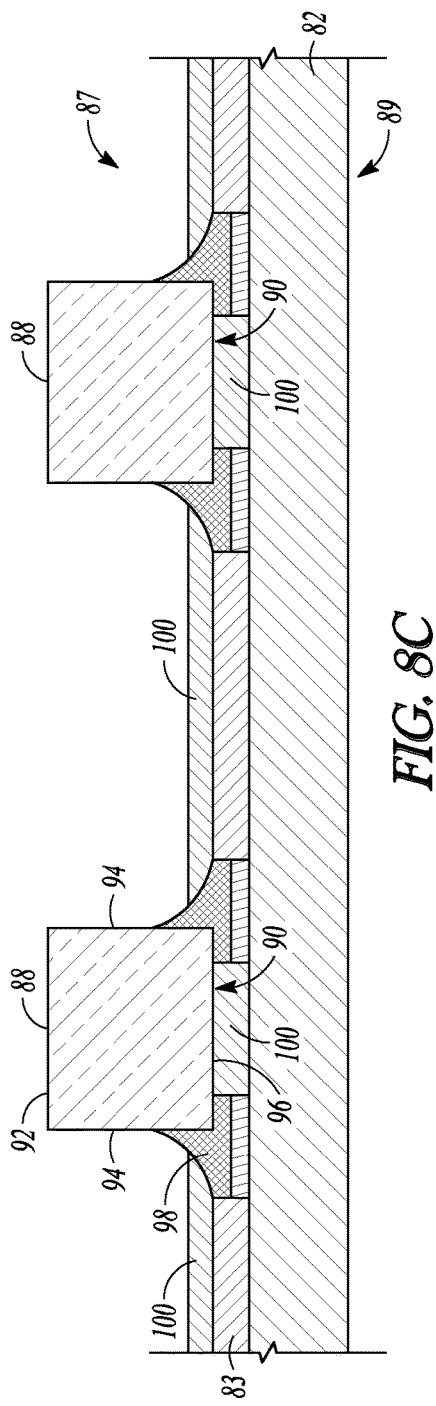
FIG. 8C illustrates an example of the first non-conductive material deposited onto the PCB in FIGS. 8A-8C

FIG. 8C illustrates an example of the first non-conductive material 100 deposited onto the PCB 82. The first non-conductive material 100 can be deposited onto the PCB 82 such that a portion of the first non-conductive material 100 flows (e.g., wicks) into the gap 90 to underfill the capacitors 88. As discussed herein, due to the confined space between the capacitors 88 and the PCB 82, the viscosity and temperature of the first non-conductive material 100 should be sufficient to enable the first non-conductive material 100 to be wicked into the gap 90.

In some examples, the first non-conductive material can be a curable epoxy resin. In that instance, prior to curing the first non-conductive material 100, the mold 102 can be located with respect to the PCB 82. The mold 102 can be located with respect to the PCB 82 such that openings 103 of the mold 102 receive a corresponding capacitor 88 or capacitors 88. Once the mold 102 is located with respect to the PCB 82, the first non-conductive material 100 can be cured to couple the mold 102 to the PCB 82. In some examples, the first non-conductive material can be deposited under the capacitors 88 and another non-conductive material can be used to couple the mold 102 to the PCB 82. In that instance, the first non-conductive material can be cured prior to depositing the other non-conductive material or the first non-conductive material can be cured concurrently with the other non-conductive material.

Figure 8D:
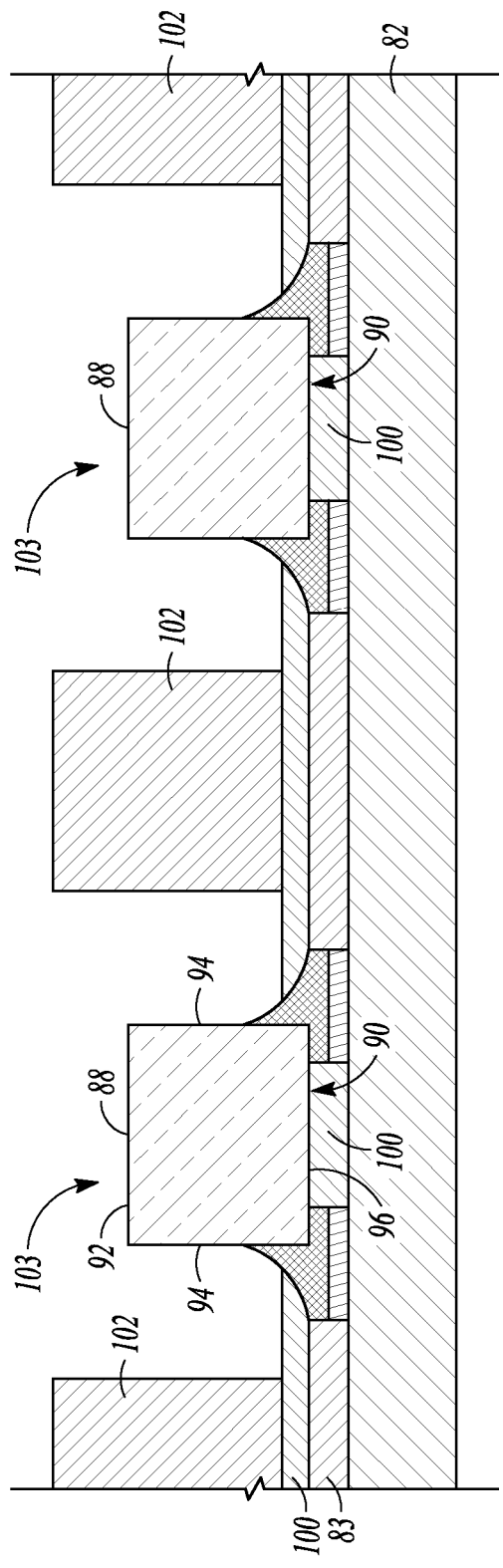
FIG. 8D illustrates a mold coupled to the PCB in FIG. 8C.
Figure 8E:
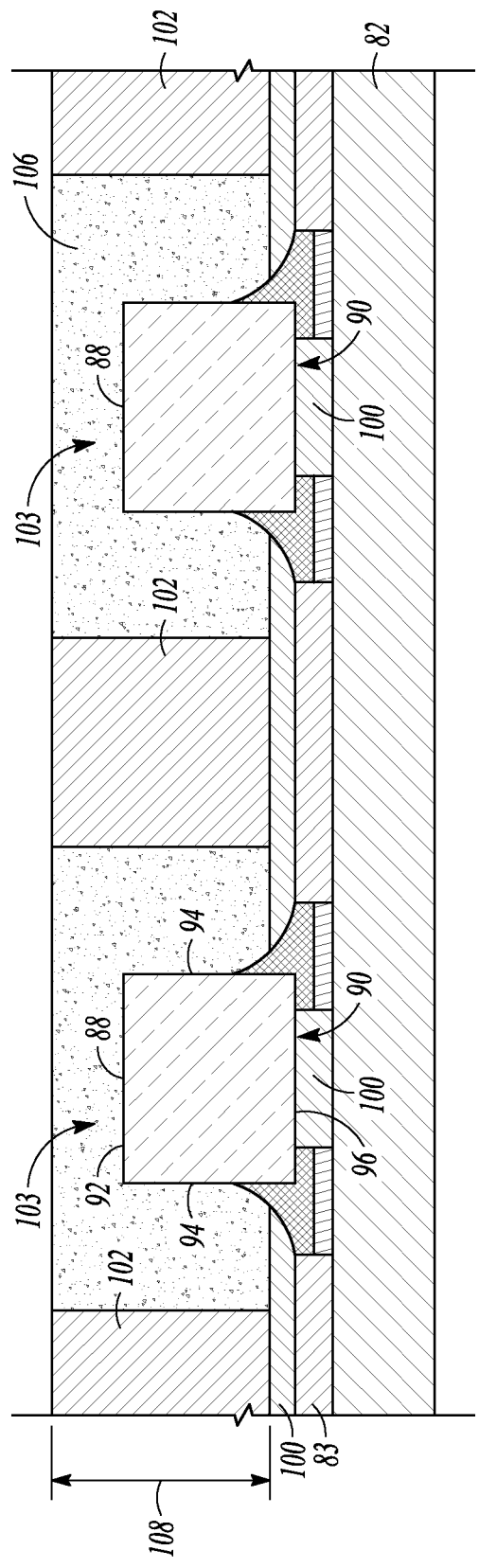
FIG. 8E illustrates an example of the mold in FIG. 8D backfilled with a second non-conductive material to encapsulate the capacitors.

FIG. 8D illustrates an example of the mold 102 having been located with respect to the PCB 102 such that a capacitor 88 is positioned within a corresponding opening 103 of the mold 102. FIG. 8E illustrates an example of the mold 102 having been backfilled with a second non-conductive material 106 to encapsulate the capacitors 88. For example, once the mold 102 is coupled to the PCB 82, the openings 103 of the mold 102 can be backfilled with the second non-conductive material 106 to encapsulate the capacitors 88. As shown in FIG. 8D, the height 108 of the mold 102 extends beyond the top surface 92 of the capacitors 88 to ensure that when the mold 102 is backfilled, the capacitor 88 will be completely encapsulated. That is, the bottom surface 96, the top surface 92, and the side surfaces 94 are encapsulated by the first and the second non-conducting materials 100, 106. The underfilled and encapsulated capacitors 88, along with the mold 102 can provide an encapsulated filtered feedthrough assembly with a high degree of dielectric isolation and can mitigate the high electric field breakdown issues associated with the electric field compression in confined spaces. While the mold 102 can provide shielding between capacitors 88, the first non-conductive material 100 and the second non-conductive material 106 used to underfill and encapsulate the capacitors act to further mitigate high voltage fields that may be present surrounding the capacitor. Thus, underfilling and encapsulating the capacitors 88 can minimize air gaps around the capacitors and increase the dielectric isolation.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A method of making an encapsulated filtered feedthrough assembly for an implantable medical device, the method comprising:
   coupling a capacitor to a printed circuit board, wherein a gap is formed between a first surface of the printed circuit board and a second surface of the capacitor;
   disposing a feedthrough conductor through the printed circuit board;
   introducing a first non-conductive material into the gap to at least partially underfill the capacitor with the first non-conductive material;
   locating a mold with respect to the printed circuit board, the mold including an opening configured to receive at least a portion of the capacitor when the mold is in location with respect to the printed circuit board; and
   introducing a second non-conductive material into the mold to encapsulate the at least a portion of the capacitor.

2. The method of claim 1, wherein coupling the capacitor to the printed circuit board includes coupling a plurality of capacitors to the printed circuit board, and wherein the mold includes a plurality of openings, each opening separated from each other and configured to receive at least a portion of at least one corresponding capacitor of the plurality of capacitors when the mold is in location with respect to the printed circuit board.

3. The method of claim 1, wherein introducing the first non-conductive material into the gap includes:

introducing the first non-conductive material onto the first surface of the printed circuit board; and allowing the first non-conductive material introduced onto the printed circuit board to be wicked into the gap.

4. The method of claim 1, further including:

coupling the feedthrough conductor to the printed circuit; and coupling the mold to the printed circuit board using the first non-conductive material.

5. The method of claim 1, wherein the mold is formed of a third non-conductive material.

6. The method of claim 5, wherein the first non-conductive material and the second non-conductive material are a different type of material from the third non-conductive material.

7. The method of claim 5, wherein the third non-conductive material includes silicone and the first non-conductive material and the second non-conductive material include a curable epoxy resin.

8. The method of claim 1, further including:

curing the first non-conductive material; and curing the second non-conductive material.

9. The method of claim 1, wherein the first and second non-conductive materials are the same.

10. The method of claim 1, wherein the first non-conductive material is different from the second non-conductive material.

\* \* \* \* \*